(12) United States Patent
Ye et al.

(10) Patent No.: US 10,590,764 B2
(45) Date of Patent: Mar. 17, 2020

(54) DETERMINING OIL CONTENT OF SOLIDS RECOVERED FROM A WELLBORE

(71) Applicant: Halliburton Energy Services, Inc., Houston, TX (US)

(72) Inventors: Xiangnan Ye, Cypress, TX (US); Dale E. Jamison, Humble, TX (US); Cato Russell McDaniel, The Woodlands, TX (US); Katerina V. Newman, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 39 days.

(21) Appl. No.: 15/555,930

(22) PCT Filed: Apr. 2, 2015

(86) PCT No.: PCT/US2015/024125
§ 371 (c)(1),
(2) Date: Sep. 5, 2017

(87) PCT Pub. No.: WO2016/160021
PCT Pub. Date: Oct. 6, 2016

(65) Prior Publication Data
US 2018/0045044 A1 Feb. 15, 2018

(51) Int. Cl.
*E21B 49/02* (2006.01)
*G01V 9/00* (2006.01)
(Continued)

(52) U.S. Cl.
CPC ............ *E21B 49/005* (2013.01); *B01D 21/30* (2013.01); *E21B 21/065* (2013.01); *E21B 47/00* (2013.01);
(Continued)

(58) Field of Classification Search
CPC ...... E21B 49/005; E21B 21/065; E21B 47/00; E21B 49/02; E21B 21/06; E21B 21/066;
(Continued)

(56) References Cited

U.S. PATENT DOCUMENTS 3,319,713 A * 5/1967 Moore .................... E21B 43/16
166/245
4,575,260 A * 3/1986 Young ................. G01N 27/185
374/136
(Continued)

FOREIGN PATENT DOCUMENTS

EP 2444802 4/2012

OTHER PUBLICATIONS

Hans-Dieter Vosteen et. al; "Influence of temperature on thermal conductivity, thermal capacity and thermal diffusivity for different types of rock", Physics and Chemistry of the Earth, vol. 28, published 2003, pp. 499-509. (Year: 2003).*
(Continued)

*Primary Examiner* — Joseph W Drodge
(74) *Attorney, Agent, or Firm* — Tenley Krueger; C. Tumey Law Group PLLC

(57) ABSTRACT

A method for the determination of the oil content for solids recovered from a wellbore is provided. The method comprises providing the solids recovered from the wellbore and measuring the thermal conductivity of the solids recovered from the wellbore using a thermal conductivity probe. The method further comprises using the thermal conductivity measurement to determine the oil content in the solids recovered from the wellbore.

16 Claims, 5 Drawing Sheets

(51) Int. Cl.
   G01N 33/24    (2006.01)
   E21B 47/00    (2012.01)
   B01D 21/30    (2006.01)
   B01D 21/34    (2006.01)
   E21B 49/00    (2006.01)
   E21B 21/06    (2006.01)

(52) U.S. Cl.
   CPC ........... *E21B 49/02* (2013.01); *G01N 33/241* (2013.01); *G01V 9/00* (2013.01)

(58) Field of Classification Search
   CPC .. E21B 47/06; E21B 47/065; E21B 2049/085; B01D 21/30; B01D 21/34; G01N 33/241; G01N 25/00; G01N 25/18; G01N 25/20; G01N 33/2823; G01V 9/00; G01V 9/005
   USPC .............. 73/152.01, 152.02, 152.04, 152.12, 73/152.13; 175/66, 206, 207; 210/742, 210/747.1, 170.01, 149; 374/10, 12, 29, 374/45, 136
   See application file for complete search history.

(56) References Cited

U.S. PATENT DOCUMENTS

| | | | | |
|---|---|---|---|---|
| 4,575,261 A * | 3/1986 | Berger | ................. | E21B 47/065 340/870.17 |
| 4,635,735 A * | 1/1987 | Crownover | ........... | E21B 21/067 175/42 |
| 4,886,118 A * | 12/1989 | Van Meurs | ............. | E21B 36/04 166/245 |
| 4,977,319 A | 12/1990 | Supernaw | | |
| 4,990,773 A | 2/1991 | Supernaw et al. | | |
| 5,201,219 A | 4/1993 | Bandurski et al. | | |
| 5,321,612 A * | 6/1994 | Stewart | ................... | G01V 1/00 374/136 |
| 5,686,724 A | 11/1997 | Spilket et al. | | |
| 8,936,700 B2 | 1/2015 | Newman et al. | | |
| 2004/0244970 A1* | 12/2004 | Smith, Jr. | ................. | E21B 7/14 166/250.01 |
| 2013/0094624 A1* | 4/2013 | Skibin | ................. | G01N 23/046 378/4 |
| 2013/0341008 A1* | 12/2013 | Brady | ................ | E21B 47/1005 166/250.01 |
| 2015/0360241 A1* | 12/2015 | Newman | ................. | B04B 13/00 494/1 |
| 2015/0377020 A1* | 12/2015 | Kronenberger | ....... | E21B 21/065 210/739 |
| 2016/0238526 A1* | 8/2016 | Fadaei | ............... | G01N 33/2823 |

OTHER PUBLICATIONS

D. A. Galson et al, "A Comparison of the Divided-Bar and QTM Methods of Measuring Thermal Conductivity", Geothermics, vol. 16, Issue No. 3, pp. 215-226, pp. 215-226. (Year: 1987).*
International Search Report and Written Opinion for PCT/US2015/024125 dated Dec. 10, 2015.
Examination Report from Australian Application No. 2015390052 dated Jan. 11, 2019.
Prats, M., "The Thermal Conductivity and Diffusivity of Green River Oil Shales", Journal of Petroleum Technology, 1975.
Dubow, J. et al., "Electrical and Thermal Transport Properties of Green River Oil Shale Heated in Nitrogen", 10th Oil Shale Symposium Proceedings, Colorado School of Mines, 1977.
Smith, J., "Specific Gravity-Oil Yield Relationships of Two Colorado Oil-Shale Cores", Industrial and Engineering Chemistry vol. 48, No. 3, 1956.
Examination Report for AU Application No. 2015390052 dated Jul. 4, 2019.

* cited by examiner

DETERMINING OIL CONTENT OF SOLIDS RECOVERED FROM A WELLBORE

BACKGROUND

Provided are systems and methods for determining the oil content of wellbore solids. More particularly, systems and methods may be provided for a real-time analysis of the oil in solids that have been recovered from a wellbore.

During the drilling of a wellbore into a subterranean formation, a drilling fluid, also referred to as a drilling mud, may be continuously circulated from the surface down to the bottom of the wellbore being drilled and back to the surface again. The drilling fluid serves several functions, one of them being to transport wellbore cuttings up to the surface where they are separated from the drilling fluid. Additionally, other solids present in the wellbore or added to the drilling fluid may also be transported and/or circulated in and/or out of the wellbore. These solids may comprise an amount of oil, either from the drilling fluid itself or from hydrocarbons native to the wellbore. The oil content of these solids is important for a variety of downstream reasons, such as disposal, efficacy of solids control equipment, etc. For these reasons and others, it may be important to precisely know the oil content of the solids recovered from a wellbore.

Determining the oil content of solids recovered from a wellbore may be useful for an efficient drilling operation. For example, the oil content may allow operators of a drilling operation to determine the method of solids disposal, price of solids disposal, the efficacy of the solids control equipment, changes to the downhole formation, filtration characteristics or requirements, etc. For example, recovered solids comprising a large volume of oil may require expensive disposal methods since the amount of oil which may be disposed of may be regulated. As another example, solids comprising a large volume of oil, may indicate that the solids control equipment is not performing in a sufficient manner. A correctly used and maintained solids control system may be necessary to maintain the drilling fluid which ensures that additional recovered solids, such as drill cuttings, make it to the surface.

Typically, the oil content of recovered solids has been measured using a technique called a retort. A retort uses a distillation unit to heat and then distill the oil in a recovered solid. The volume fraction may then be compared to a baseline if known or used to establish a baseline. This process can take an hour or more. As such, the retort process is slower to perform and may provide measurements that lag relative to the operation. The retort measurements only illustrate the oil content of the solid when the sample was taken. This may lead to delayed correction of an errant process and a reduction in the overall efficiency of the operation.

BRIEF DESCRIPTION OF THE DRAWINGS

These drawings illustrate certain aspects of some examples of the present invention, and should not be used to limit or define the invention.

DETAILED DESCRIPTION

Figure 1:
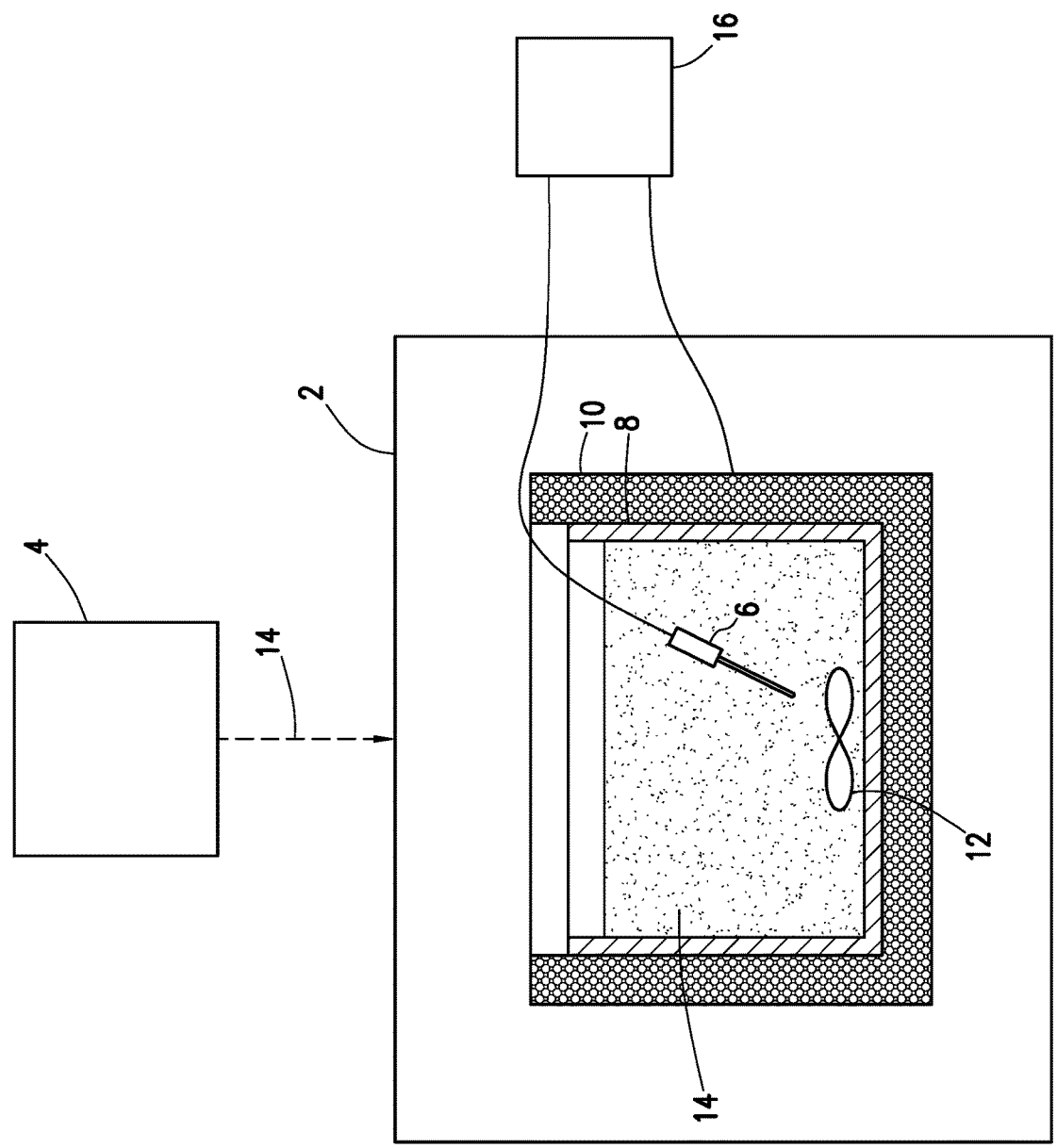
FIG. 1 is a schematic diagram using an example recovered solid monitoring and handling system.

Provided are systems and methods for determining the oil content of wellbore solids. More particularly, systems and methods may be provided for a real-time analysis of the oil in solids that have been recovered from a wellbore.

As disclosed below, systems and methods may be provided for determining the oil content of solids recovered from a wellbore. Solids recovered from a wellbore, herein referred to as "recovered solids," generally includes any solids removed from a wellbore, which may include solids removed from the surface of a wellbore or solids removed from within a wellbore. Examples of recovered solids may include, but should not be limited to, drill cuttings, solid drilling fluid additives such as weighting agents, lost-circulation materials, etc.; proppants; solids native to the subterranean formation which may include sand, minerals, etc.; the like; or any combinations thereof. As the recovered solids are introduced to and/or circulated within the wellbore, the recovered solids may contact oil and be contaminated with the oil. The oil may be from the drilling fluid, for example, if the drilling fluid is an oil-based mud ("OBM"), where oil is the continuous phase and water, brine, or other non-miscible material is the internal phase. The oil may also be native to the subterranean formation, for example, hydrocarbons present within the subterranean formation being drilled into. The oil may also come from other treatment or wellbore fluids introduced into the wellbore and/or subterranean formation.

With any recovered solid comprising oil, the amount of oil present may impact the thermal conductivity of the recovered solid. Since the oil and the recovered solids have different capabilities of conducting heat, the thermal conductivity of a recovered solid may be measured and compared with a calibration curve or other known baseline to determine the oil content of a recovered solid or the relative changes to the oil content in recovered solids during an active drilling operation. Thus, the thermal conductivity of recovered solids may be standardized, such that the measurement of the thermal conductivity of a recovered solid may be taken in real-time and compared to this standardization to ascertain the oil content of a recovered solid. Advantageously, the systems and methods disclosed herein may allow an operator or an automated process to quickly and efficiently ascertain a recovered solid's oil content and then adjust the solids control equipment to counter changes in the oil content of the recovered solids. This may make it possible to improve reactivity times for drilling fluid adjustments and to monitor the efficacy of solids control equipment during a drilling operation.

A method to determine an oil content for solids recovered from a wellbore may be provided. The method may include one or all of the components and/or steps illustrated in FIGS. 1-5. The method may comprise providing the solids recovered from the wellbore; measuring the thermal conductivity of the solids recovered from the wellbore using a thermal conductivity probe; and using the thermal conductivity measurement to determine the oil content in the solids recovered from the wellbore. The solids recovered from the wellbore may comprise drill cuttings. The thermal conductivity probe may be a needle probe. The method may further comprise heating the solids recovered from the wellbore. The method may further comprise placing the solids recovered from the wellbore in a vessel and pressuring the vessel. The method may further comprise recording measurements obtained from the thermal conductivity probe. The method may further comprise separating the solids from a drilling fluid. The method may further comprise using the oil content to adjust a parameter of a solids control system; the solids control system being used in the step of separating the solids from the drilling fluid. The method may further comprise recovering the solids from the wellbore.

A method to determine an oil content for solids recovered from a wellbore may be provided. The method may include one or all of the components and/or steps illustrated in FIGS. 1-5. The method may comprise placing the solids recovered from the wellbore in a vessel; measuring the thermal conductivity of the solids recovered from the wellbore using a thermal conductivity probe; and comparing the measured thermal conductivity to predetermined thermal conductivity data correlated with a known oil content to determine the oil content of the solids. The solids recovered from the wellbore may comprise drill cuttings. The thermal conductivity probe may be a needle probe. The method may further comprise heating the solids recovered from the wellbore. The method may further comprise placing the solids recovered from the wellbore in a vessel and pressuring the vessel. The method may further comprise recording measurements obtained from the thermal conductivity probe. The method may further comprise separating the solids from a drilling fluid. The method may further comprise using the oil content to adjust a parameter of a solids control system; the solids control system being used in the step of separating the solids from the drilling fluid. The method may further comprise recovering the solids from the wellbore.

A system for determining an oil content for solids recovered from a wellbore may be provided. The system may include one or all of the components and/or steps illustrated in FIGS. 1-5. The system may comprise a vessel, a heating element capable of heating the vessel, a mixing element disposed within the vessel, a thermal conductivity probe disposed within the vessel, and a control unit coupled to the thermal conductivity probe. The system may further comprise a solids control system coupled to the vessel. The control unit may be coupled to the heating element and the mixing element. The solids recovered from the wellbore may comprise drill cuttings. The thermal conductivity probe may be a needle probe.

Referring now to FIG. 1, a diagram is shown generally depicting an offline recovered solid monitoring and handling system 2 for monitoring the oil content of recovered solids. As illustrated, a portion of recovered solids may be removed from solids control system 4 or may be supplied to the recovered solid monitoring and handling system 2 from any other source as desired. The portion of recovered solids may be added to the recovered solid monitoring and handling system 2 automatically or manually as desired. The recovered solid monitoring and handling system 2 may comprise a thermal conductivity probe 6, a vessel 8, a heating element 10, and an optional mixing element 12. As illustrated, vessel 8 may contain a sample of recovered solids 14. Vessel 8 is illustrated as a beaker in FIG. 1. The thermal conductivity probe 6, illustrated in FIG. 1 as a needle probe, may be inserted into a sample of recovered solids 14. Heating element 10, illustrated in FIG. 1 as a heating jacket, may be used to heat the sample of recovered solids 14. Mixing element 12 may be used to mix the sample of recovered solids 14. Thermal conductivity probe 6 may be coupled to a control unit 16. Control unit 16 may be used to control the activity and functionality of thermal conductivity probe 6. Further, control unit 16 may record the measurements of the thermal conductivity probe 6 and, in some examples, provide analysis of the collected measurements. In some examples, control unit 16 may be coupled to heating element 10 and mixing element 12. In these examples, control unit 16 may be used to control heating element 10 and mixing element 12.

With continued reference to FIG. 1, a portion of recovered solids 14 may be inserted into vessel 8. A thermal conductivity probe 6 may then be inserted into the portion of recovered solids 14. Vessel 8 may then be pressurized to provide consistency over measurements. Control unit 16 may then initiate heating of vessel 8 and mixing of the recovered solids 14 via heating element 10 and mixing element 12. Control unit 16 may then initiate the measurement and subsequent recording of the thermal conductivity of the recovered solids through activation of thermal conductivity probe 6. If desired, control unit 16 may be used to alter the testing parameters in real-time and may also provide real-time analysis of the thermal conductivity data.

The thermal conductivity probe 6 may be any thermal conductivity probe suitable for measuring the thermal conductivity of recovered solids 14 comprising oil. Thermal conductivity probes 6 may include steady state probes and unsteady state probes. Examples of which may include, but should not be limited to, needle probes, button probes, strip probes, plate sensor, and the like. Methods of measuring thermal conductivity may include the divided bar method, transient plane source method, transient line source method, laser flash method, the 3ω-method, the time-domain thermoreflectance method, and any other suitable method of measuring thermal conductivity of the recovered solids 14.

The vessel 8 may be any vessel sufficient for containing the recovered solids 14. Examples of vessel 8 may include a test tube, a beaker, a flask, a barrel, a drum, a tray, and the like. Vessel 8 may be made of any material sufficient for containing recovered solids 14. Vessel 8 may be coupled to heating element 10 and/or mixing element 8. Vessel 8 may be pressurized to maintain a constant pressure. With the benefit of this disclosure, one of ordinary skill in the art will be able to select a vessel 8 for a desired application.

The heating element 10 may be any heating element sufficient for heating vessel 8 and for raising the temperature of the recovered solids 14 to a desired temperature. Examples of heating element 10 may include heating jackets, hot plates, burners, and the like. Heating element 10 may be coupled to vessel 8 and/or control unit 16. Control of heating element 10 may be performed manually or automatically. Heating element 10 may be controlled by control unit 16 in examples where heating element 10 is coupled to control unit 16. With the benefit of this disclosure, one of ordinary skill in the art will be able to select a heating element 10 for a desired application.

The mixing element 12 may be any mixing element sufficient for mixing the recovered solids 14 to a desired level. In the offline recovered solid monitoring and handling system 2 described by FIG. 1, the mixing element is optional. Examples of mixing element 12 may include a bob with sleeve, a stirring bar, a blade, and the like. Mixing element 12 may be coupled to vessel 8 and/or control unit 16. Control of mixing element 12 may be performed manually or automatically. Mixing element 12 may be controlled by control unit 16 in examples where mixing element 12 is coupled to control unit 16. With the benefit of this disclosure, one of ordinary skill in the art will be able to select a mixing element 12 for a desired application.

Recovered solids 14 may be any solids recovered from a wellbore. Recovered solids 14 may include solids removed from the surface of a wellbore or solids removed from within a wellbore. Examples of recovered solids 14 may include, but should not be limited to, drill cuttings, solid drilling fluid additives such as weighting agents, lost-circulation materials, etc.; proppants; solids native to the subterranean formation which may include sand, minerals, etc.; the like; or any combinations thereof. Recovered solids 14 may contact and thus comprise oil. "Oil" as used herein is used to represent any nonaqueous fluid which may contact the recovered solids 14. The recovered solids 14 may contact oil from a drilling fluid, other treatment fluid, from a subterranean formation, or from any combination thereof. Examples of nonaqueous fluids may include hydrocarbon liquids or more generally any product obtained from oil such as diesel oil or mineral oil. Further, the term nonaqueous fluid also encompasses synthetic muds or any nonaqueous fluid that is analogous to oil muds and may be analyzed using the methods and systems described herein.

Control unit 16 may conduct and/or perform the analysis of the recovered solids 14 using thermal conductivity probe 6. Control unit 16 may be coupled to thermal conductivity probe 6. In optional examples, control unit 16 may be couple to heating element 10 and/or mixing element 12. In further optional examples, control unit 16 may be coupled to solids control system 4. Control unit 16 may include a direct connection, a private network, a virtual private network, a local area network, a WAN (e.g., an Internet-based communication system), a wireless communication system (e.g., a satellite communication system, telephones), combinations thereof, or any other suitable communication link. Control unit 16 may be any suitable data processing system, including computer systems, handheld devices, or any other suitable device. A suitable data processing system may include a processor, memory, and software operable on the processor to process and analyze the measurement data generated by the thermal conductivity probe 6, to adjust the parameters of the heating element 10 and/or mixing element 12, and/or operate any part or the whole of the recovered solid monitoring and handling system 2. Control unit 16 may optionally comprise a method and/or component for data storage, which may comprise any device suitable for storing data to be processed, including, but not limited to, compact disc drives, floppy drives, hard disks, flash memory, solid state drives, and the like. Those of ordinary skill in the art will appreciate that suitable data processing systems may comprise additional, fewer, and/or different components than those described for control unit 16.

Data processing and analysis software used with control unit 16 may be used to analyze the data generated by thermal conductivity probe 6. This procedure may be automated such that the analysis happens without the need for operator input or control. Further, the operator may select from several previously input parameters or may be able to recall previously measured data. Any of the data may be transferable and/or storable on a USB or any other type of drive if desired.

Figure 2:
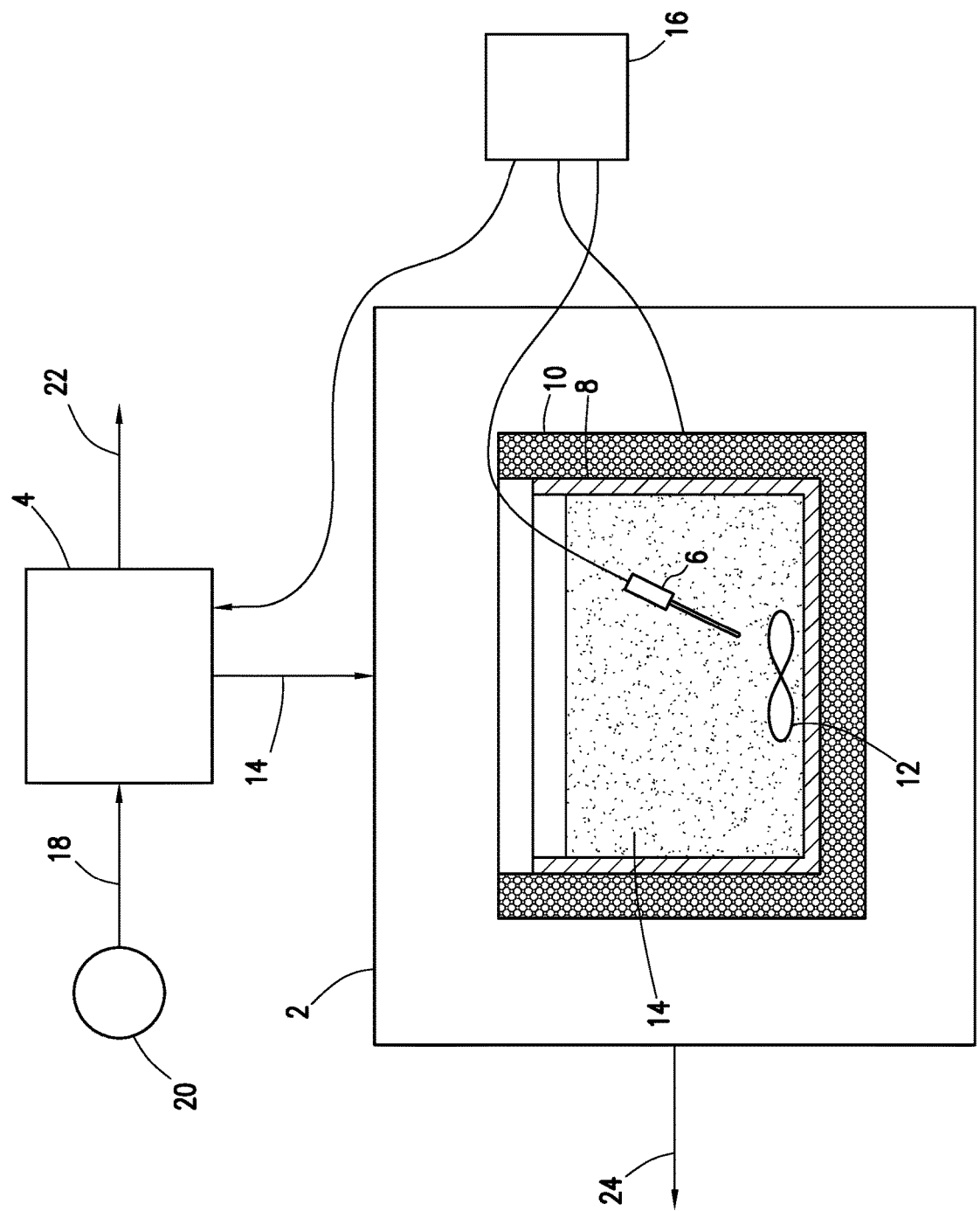
FIG. 2 is schematic diagram of another example of a recovered solid monitoring and handling system.

Referring now to FIG. 2, a diagram is shown generally depicting an inline recovered solid monitoring and handling system 2 for monitoring the oil content of recovered solids 14. As illustrated, circulated drilling fluid 18 from wellbore 20 may be conveyed to solids control system 4. Solids control system 4 may include various methods and systems for solids control, examples of which may include but are not limited to, one or more of a shaker (e.g., shale shaker), a centrifuge, a hydrocyclone, a separator (including magnetic and electrical separators), a desilter, a desander, a separator, a filter (e.g., diatomaceous earth filters), a heat exchanger, and any fluid reclamation equipment. Solids control system 4 may remove and separate recovered solids from the circulated drilling fluid 18. After such removal, a clean drilling fluid 22 may be transported to a mud pit or for further downstream processing. The recovered solids 14 may be removed from the solids control system 4 as they are accumulated and then added to the recovered solid monitoring and handling system 2. The recovered solids 14 may be added to the recovered solid monitoring and handling system 2 automatically or manually as desired. The recovered solid monitoring and handling system 2 may comprise a thermal conductivity probe 6, a vessel 8, an optional heating element 10, and an optional mixing element 12. As illustrated, vessel 8 contains a sample of recovered solids 14. Vessel 8 is illustrated as a beaker in FIG. 2. The thermal conductivity probe 6, illustrated in FIG. 2 as a needle probe, may be inserted into the recovered solids 14. Heating element 10, illustrated in FIG. 1 as a heating jacket, may be used to heat the sample of recovered solids 14. Mixing element 12 may be used to mix the recovered solids 14. In the inline recovered solid monitoring and handling system 2 described by FIG. 2, both the heating element 10 and the mixing element 12 may be optional.

Although thermal conductivity probe 6 is illustrated as being inserted into vessel 8, where vessel contains recovered solids 14, it is to be understood that in the inline recovered solid monitoring and handling system 2 described by FIG. 2, thermal conductivity probe 6 may be used at any location in a drilling system (e.g., drilling system 26 described in FIG. 4 below) where the thermal conductivity probe could be placed to measure the thermal conductivity of the recovered solids. This placement may include placement in an upstream or downstream process of the solids control system 4. For example, the thermal conductivity probe 6 may be placed in-line in any process line. The thermal conductivity probe 6 must be in contact with the recovered solids 14 to be measured, but the thermal conductivity probe 6 may be enclosed inside piping or a vessel 8 or placed pipes and vessels 8 open to the atmosphere. Thus the examples disclosed herein expressly contemplate the use of a thermal conductivity probe 6 to measure the thermal conductivity of the solids at any point in the drilling operation after the solids have been recovered from the wellbore. With the benefit of this disclosure, one of ordinary skill in the art will be able to determine an appropriate placement for the thermal conductivity probe 6. Further, the examples disclosed herein expressly contemplate the use of multiple thermal conductivity probes 6 to make multiple thermal conductivity measurements of the recovered solids 14 as the recovered solids 14 progress through a drilling system (e.g., drilling system 26, as described in FIG. 4 below). These multiple measurements may be used for any variety of reasons as would occur to one of ordinary skill in the art. With the benefit of this disclosure, one of ordinary skill in the art will be able to determine whether multiple thermal conductivity probes 6 may be used for a desired application.

Thermal conductivity probe 6 may be coupled to a control unit 16. Control unit 16 may be used to control the activity and functionality of thermal conductivity probe 6. Further, control unit 16 may record the measurements of the thermal conductivity probe 6 and, in some examples, provide analysis of the collected measurements. In some examples, control unit 16 maybe coupled to heating element 10, mixing element 12, and/or solids control system 4. In these examples, control unit 16 may be used to control heating element 10 and/or mixing element 12, and may also be used to alter parameters of solids control system 4.

Using the thermal conductivity probe 6 as described above, the control unit 16 may record the measurements of the thermal conductivity probe 6 as they are produced and in optional examples, may analyze the thermal conductivity measurements. The measurement of thermal conductivity, recordation, and analysis processes may be automated in part or in whole. Alternatively, the processes may not be automated. Further the analysis process may provide feedback for the adjustment of one or more parameters of the solids control system 4. For example, the results of the analysis performed by control unit 16 may indicate that adjustment should be made at an upstream or downstream process within or external to the solids control system 4. Such adjustment may be automated in part or in whole. Alternatively, said adjustment may not be automated.

Figure 3:
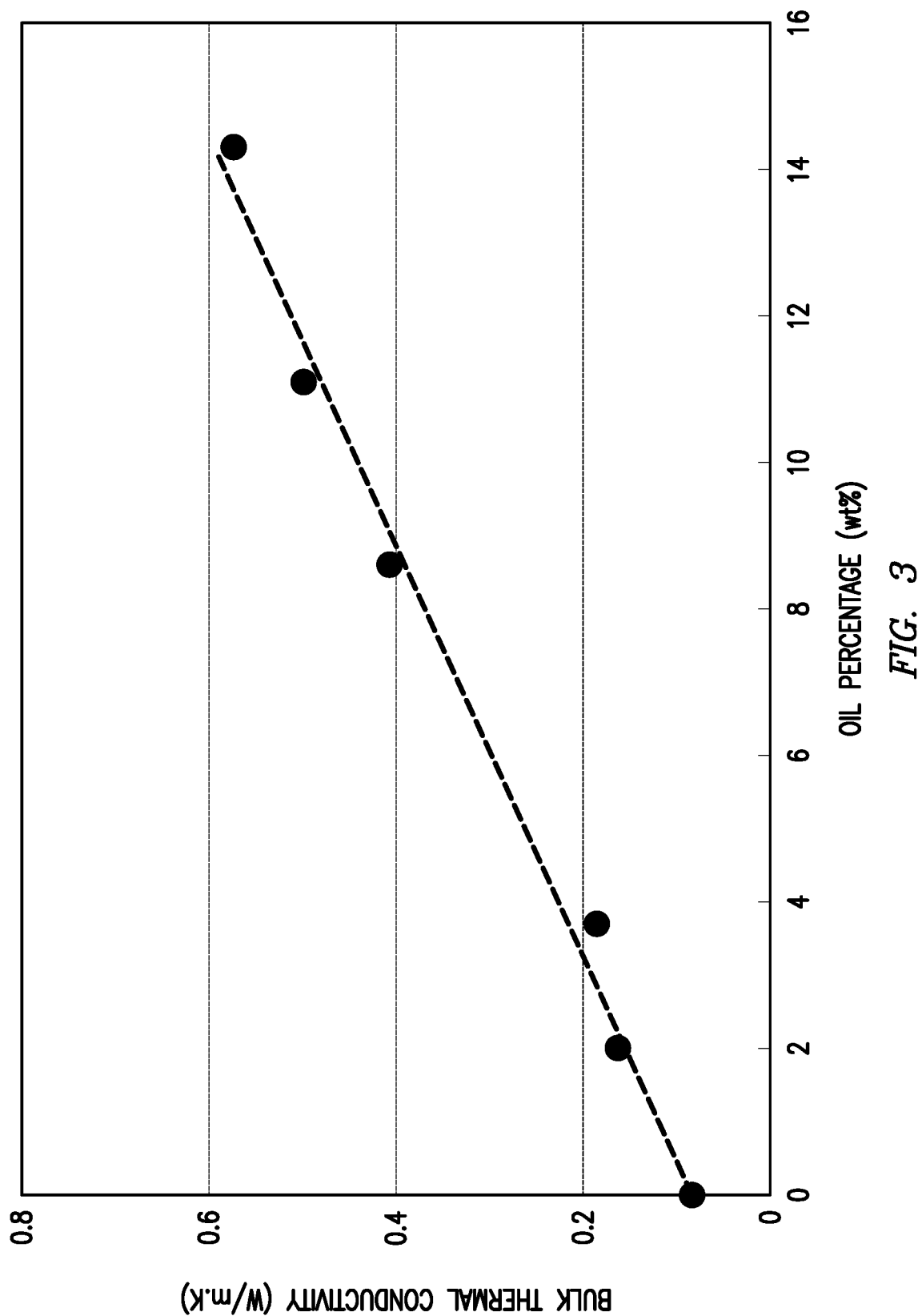
FIG. 3 illustrates an example calibration curve for the measurement of the oil content of recovered solids using the bulk thermal conductivity of the recovered solids.

The measurement of the thermal conductivity of the recovered solids 14 may be recorded and compared to a calibration curve. The calibration curve may comprise plotted data points obtained from measuring the thermal conductivity for a specific formulation of a drilling fluid in which the oil content was varied at desired intervals. A curve may then be fit to these data points. A measured thermal conductivity for a matching drilling fluid formulation may be compared to this calibration curve to find the corresponding oil content of the recovered solids. FIG. 3 illustrates an example calibration curve illustrating a linear relationship with a best fit of Y=0.0358X+0.0834. As illustrated, for known formulations, the measurement of the bulk thermal conductivity in the recovered solids may be related to the oil content in the recovered solids. A calibration curve may be used to cross reference a measured thermal conductivity value with predetermined thermal conductivity values that correspond to known oil content measurements. Thus, the calibration curve may relate the values of one or more input parameters (e.g., thermal conductivity or recovered solids) to a corresponding output value (e.g., oil content of the recovered solids). The calibration curve may be previously prepared using data obtained from the wellbore or from similarly situated operations which may have used similar formulations of drilling fluids, or the calibration curve may be generated during a continuous operation.

In some examples, determining the oil content of the recovered solids may comprise comparing the measured thermal conductivity with predetermined thermal conductivity values via a lookup table. A "lookup table," as used herein, may include nay array, any database, any matrix, or other similar arrangement usable to cross reference data (e.g., one or more numerical values, parameters, attributes, factors, properties, etc.). Generally speaking, a lookup table may relate the values of one or more input parameters to a corresponding output value. For example, a lookup table may relate a particular value of thermal conductivity to a corresponding amount of oil content. In some examples, a two—dimensional lookup table may relate thermal conductivity measurements corresponding to a known oil formulation (e.g., the oleaginous or non-aqueous base fluid of a drilling fluid) to a specific oil content value, such that when specific values of thermal conductivity and oil formulation are input to the lookup table, the lookup table may produce a corresponding oil content value.

After the oil content of the recovered solids 14 has been determined, the recovered solids 14 may be disposed of via disposal method 24. Disposal method 24 may comprise any method of disposal sufficient for disposal of recovered solids comprising a known percentage of oil content. The disposal method 24 used may vary based on the oil content of the recovered solids 14.

Figure 4:
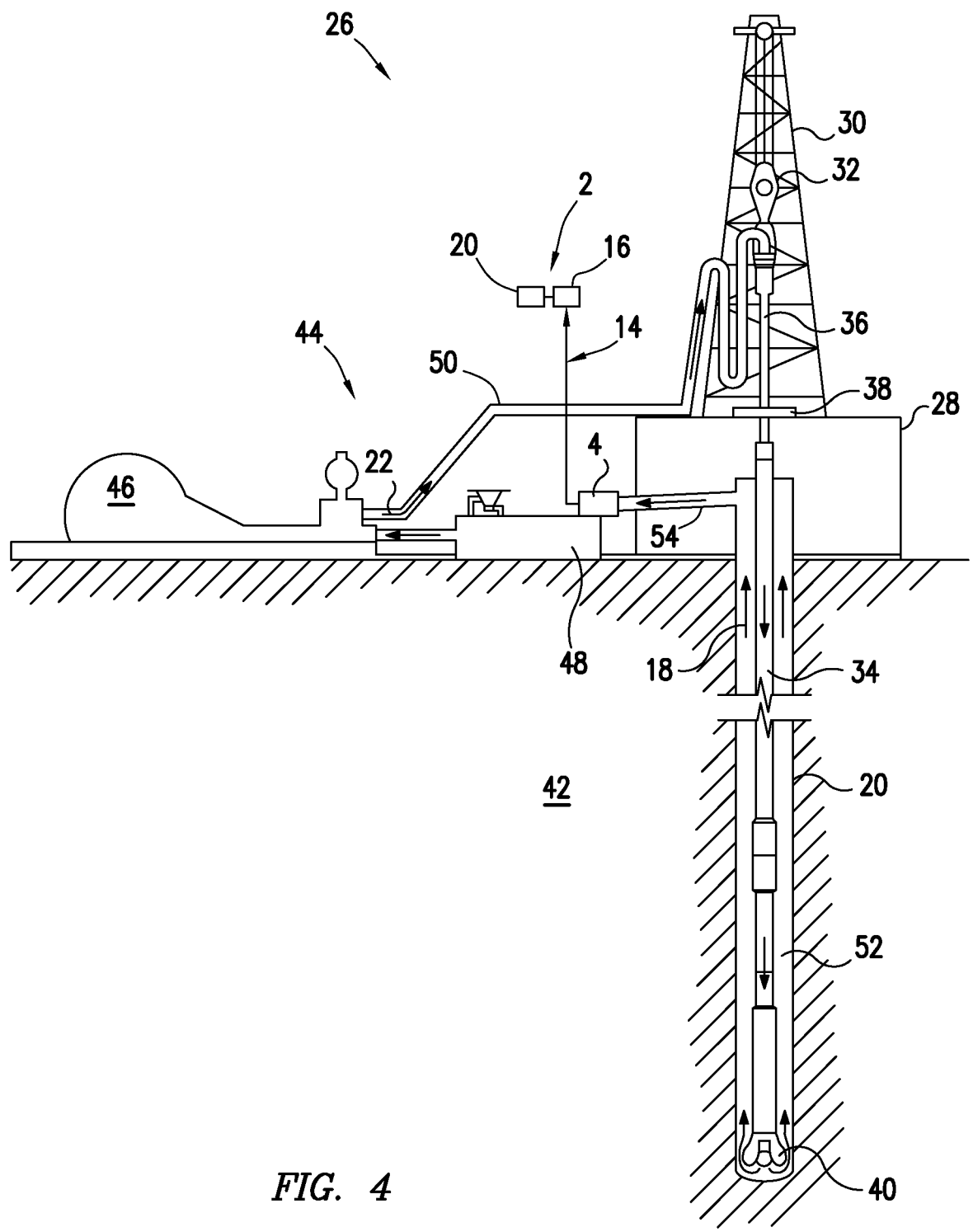
FIG. 4 is a schematic diagram of an example drilling fluid system using a recovered solid monitoring and handling system.

Referring now to FIG. 4, the disclosed recovered solid monitoring and handling system 2 may be used in conjunction with a drilling system 26. It should be noted that while FIG. 4 generally depicts a land-based drilling system, those skilled in the art will readily recognize that the principles described herein are equally applicable to subsea drilling operations that employ floating or sea-based platforms and rigs, without departing from the scope of the disclosure.

As illustrated, the drilling system 26 may include a drilling platform 28 that supports a derrick 30 having a traveling block 32 for raising and lowering a drill string 34. The drill string 34 may include, but is not limited to, drill pipe and coiled tubing, as generally known to those skilled in the art. A kelly 36 may support the drill string 34 as it may be lowered through a rotary table 38. A drill bit 40 may be attached to the distal end of the drill string 34 and may be driven either by a downhole motor and/or via rotation of the drill string 34 from the well surface. Without limitation, the drill bit 40 may include, roller cone bits, PDC bits, natural diamond bits, any hole openers, reamers, coring bits, and the like. As the drill bit 40 rotates, it may create a wellbore 20 that penetrates various subterranean formations 42.

The drilling system 26 may further include a fluid monitoring and handling system 44 comprising component parts such as mud pump 46, one or more solids control systems 4, and a mud pit 48. The mud pump 46 representatively includes any conduits, pipelines, trucks, tubulars, and/or pipes used to fluidically convey the clean drilling fluid 22 downhole, any pumps, compressors, or motors (e.g., topside or downhole) used to drive the clean drilling fluid 22 into motion, any valves or related joints used to regulate the pressure or flow rate of the clean drilling fluid 22, and any sensors (e.g., pressure, temperature, flow rate, etc.), gauges, and/or combinations thereof, and the like.

The mud pump 46 may circulate the clean drilling fluid 22 through a feed pipe 50 and to the kelly 36, which may convey the clean drilling fluid 22 downhole through the interior of the drill string 34 and through one or more orifices in the drill bit 40. The now circulated drilling fluid 18 may then be circulated back to the surface via an annulus 52 defined between the drill string 34 and the walls of the wellbore 20. At the surface, the circulated drilling fluid 18 may be conveyed to the solids control system 4 via an interconnecting flow line 54. The solids control system 4, as also described in FIGS. 1 and 2, may include various methods and systems for solids control, examples of which may include but are not limited to, one or more of a shaker (e.g., shale shaker), a centrifuge, a hydrocyclone, a separator (including magnetic and electrical separators), a desilter, a desander, a separator, a filter (e.g., diatomaceous earth filters), a heat exchanger, and any fluid reclamation equipment. Solids control system 4 may remove and separate recovered solids from the circulated drilling fluid 18 After passing through the solids control system 4, a now cleaned drilling fluid 22 may be deposited into a nearby mud pit 48. While illustrated as being arranged at the outlet of the wellbore 22 via the annulus 52, those skilled in the art will readily appreciate that the solids control system 4 may be arranged at any other location in the drilling system 26 to facilitate its proper function, without departing from the scope of the disclosure.

Referring still to FIG. 4, the fluid monitoring and handling system 10 may further include a recovered solids monitoring and handling system 2 as described above in FIGS. 1 and 2. As illustrated in FIG. 4, the recovered solids monitoring and handling system 2 comprises a vessel 8 and a disposal method 24. The vessel 8 may be disposed on a skid supported on the platform 28. The recovered solids monitoring and handling system 2 may, for example, continuously or intermittently measure the thermal conductivity of recovered solids 14, which have been recovered from the circulated drilling fluid 18. As illustrated, recovered solids 14 may be taken from the circulated drilling fluid 18 and conveyed to a vessel 8 whereby the thermal conductivity of the recovered solids may be measured using a thermal conductivity probe (as illustrated in FIGS. 1 and 2). Once the thermal conductivity has been measured, the recovered solids may be sent for disposal via disposal method 24 (as described in FIG. 2). Additionally, and as described in FIGS. 1 and 2, a control unit (such as control unit 16 as illustrated FIGS. 1 and 2) may analyze the thermal conductivity of the recorded solids 14 to determine the oil content of the recovered solids 14. The determined oil content may be used to modify elements of upstream processes such as disposal method 24 or downstream processes such as solids control unit 4 if desired.

To facilitate a better understanding of the present claims, the following examples of certain aspects of the disclosure are given. In no way should the following examples be read to limit, or define, the entire scope of the claims.

EXAMPLES

Figure 5:
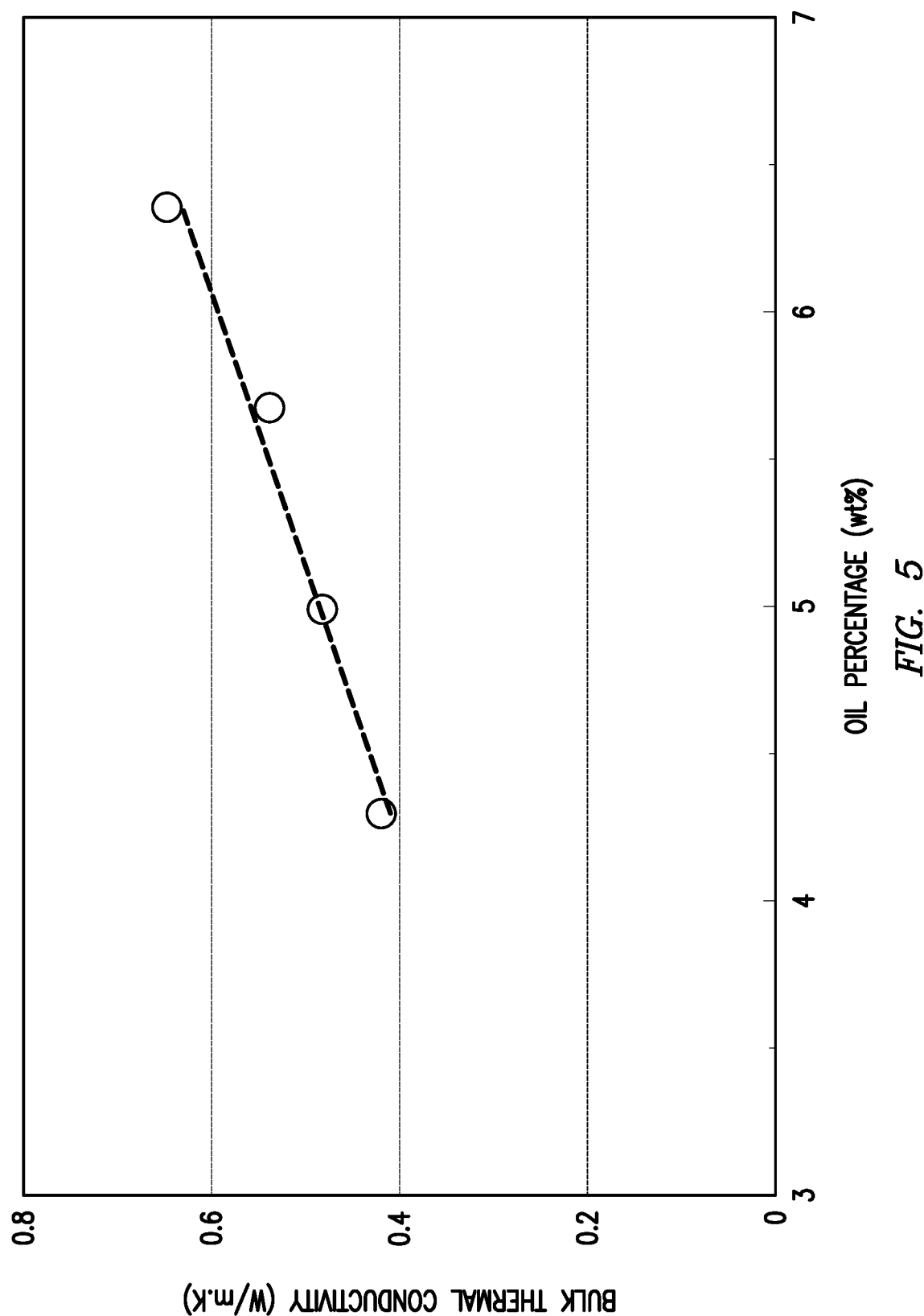
FIG. 5 illustrates an example experimental curve prepared from real recovered solids from a circulated drilling fluid.

This example illustrates that the measurement of the thermal conductivity may allow for the determination of the oil content of recovered solids from a circulated drilling fluid. FIG. 5 illustrates a plot depicting drill cuttings from an oil based mud circulated in a wellbore. The cuttings had an average diameter of 3.1 to 9.2 mm. Each data point represents a different oil percentage by weight. The best fit for the experimental data was Y=0.1073X+0.0517 and is represented by the dashed line. As shown by FIG. 5, a linear relationship exists between the bulk thermal conductivity of the recovered solids and the oil percentage by weight of the recovered solids. This relationship allows for a determination of the oil content of recovered solids by measuring the thermal conductivity of the recovered solids. Further, this information may be used to adjust equipment parameters or to determine the proper means of solids disposal.

The preceding description provides various embodiments of the systems and methods of use disclosed herein which may contain different method steps and alternative combinations of components. It should be understood that, although individual embodiments may be discussed herein, the present disclosure covers all combinations of the disclosed embodiments, including, without limitation, the different component combinations, method step combinations, and properties of the system. It should be understood that the compositions and methods are described in terms of "comprising," "containing," or "including" various components or steps, the compositions and methods can also "consist essentially of" or "consist of" the various components and steps. Moreover, the indefinite articles "a" or "an," as used in the claims, are defined herein to mean one or more than one of the element that it introduces.

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited. Additionally, whenever a numerical range with a lower limit and an upper limit is disclosed, any number and any included range falling within the range are specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values even if not explicitly recited. Thus, every point or individual value may serve as its own lower or upper limit combined with any other point or individual value or any other lower or upper limit, to recite a range not explicitly recited.

Therefore, the present embodiments are well adapted to attain the ends and advantages mentioned as well as those that are inherent therein. The particular embodiments disclosed above are illustrative only, and may be modified and practiced in different but equivalent manners apparent to those skilled in the art having the benefit of the teachings herein. Although individual embodiments are discussed, the disclosure covers all combinations of all of the embodiments. Furthermore, no limitations are intended to the details of construction or design herein shown, other than as described in the claims below. Also, the terms in the claims have their plain, ordinary meaning unless otherwise explicitly and clearly defined by the patentee. It is therefore evident that the particular illustrative embodiments disclosed above may be altered or modified and all such variations are considered within the scope and spirit of those embodiments. If there is any conflict in the usages of a word or term in this specification and one or more patent(s) or other documents that may be incorporated herein by reference, the definitions that are consistent with this specification should be adopted.

What is claimed is:

1. A method to determine an oil content for solids recovered from a wellbore, the method comprising:
   providing the solids recovered from the wellbore wherein the solids recovered from the wellbore comprise drill cuttings;
   measuring the thermal conductivity of the solids recovered from the wellbore using a thermal conductivity probe; and
   comparing the measured thermal conductivity to a known baseline to determine the oil content in the solids recovered from the wellbore.

2. A method according to claim 1, further comprising heating the solids recovered from the wellbore.

3. A method according to claim 1, further comprising placing the solids recovered from the wellbore in a vessel and pressuring the vessel.

4. A method according to claim 1, further recording measurements obtained from the thermal conductivity probe.

5. A method to determine an oil content for solids recovered from a wellbore, the method comprising:
   providing the solids recovered from the wellbore;
   measuring the thermal conductivity of the solids recovered from the wellbore using a thermal conductivity probe, wherein the thermal conductivity probe is a needle probe; and
   comparing the measured thermal conductivity to a known baseline to determine the oil content in the solids recovered from the wellbore.

6. A method to determine an oil content for solids recovered from a wellbore, the method comprising:
   providing the solids recovered from the wellbore;
   separating the solids from a drilling fluid;
   measuring the thermal conductivity of the solids recovered from the wellbore using a thermal conductivity probe; and
   comparing the measured thermal conductivity to a known baseline to determine the oil content in the solids recovered from the wellbore.

7. A method according to claim 6, further comprising using the oil content in the solids recovered from the wellbore to adjust a parameter of a solids control system, the solids control system being used in the step of separating the solids from the drilling fluid.

8. A method to determine an oil content for solids recovered from a wellbore, the method comprising:
   placing the solids recovered from the wellbore in a vessel, wherein the solids recovered from the wellbore comprise drill cuttings;
   measuring the thermal conductivity of the solids recovered from the wellbore using a thermal conductivity probe; and
   comparing the measured thermal conductivity to predetermined thermal conductivity data correlated with a known oil content to determine the oil content of the solids.

9. A method according to claim 8, further comprising heating the solids recovered from the wellbore.

10. A method according to claim 8, further comprising pressuring the vessel.

11. A method according to claim 8, recording measurements obtained from the thermal conductivity probe.

12. A method according to claim 8, further comprising recovering the solids from the wellbore.

13. A method to determine an oil content for solids recovered from a wellbore, the method comprising:
   placing the solids recovered from the wellbore in a vessel;
   measuring the thermal conductivity of the solids recovered from the wellbore using a thermal conductivity probe, wherein the thermal conductivity probe is a needle probe; and
   comparing the measured thermal conductivity to predetermined thermal conductivity data correlated with a known oil content to determine the oil content of the solids.

14. A method to determine an oil content for solids recovered from a wellbore, the method comprising:
   placing the solids recovered from the wellbore in a vessel;
   separating the solids from a drilling fluid;
   measuring the thermal conductivity of the solids recovered from the wellbore using a thermal conductivity probe; and
   comparing the measured thermal conductivity to predetermined thermal conductivity data correlated with a known oil content to determine the oil content of the solids.

15. A system for determining an oil content for solids recovered from a wellbore, the system comprising:
   a vessel,
   a heating element capable of heating the vessel,
   a mixing element disposed within the vessel,
   a thermal conductivity probe disposed within the vessel, and
   a control unit coupled to the thermal conductivity probe, wherein the control unit is configured to receive the measured thermal connectivity and compare the measured thermal connectivity to a known baseline to determine the oil content of the recovered solids.

16. The system of claim 15 wherein the control unit is coupled to the heating element and the mixing element.

* * * * *